United States Patent
Mühlbauer

(10) Patent No.: US 6,541,040 B2
(45) Date of Patent: Apr. 1, 2003

(54) MIXTURE FOR USE AS WOUND DRESSING

(75) Inventor: Wolfgang Mühlbauer, Hamburg (DE)

(73) Assignee: Ernst Milbauer KG (DE)

( * ) Notice: Subject to any disclaimer, the term of this patent is extended or adjusted under 35 U.S.C. 154(b) by 242 days.

(21) Appl. No.: 09/169,559

(22) Filed: Oct. 9, 1998

(65) Prior Publication Data

US 2001/0006674 A1 Jul. 5, 2001

(30) Foreign Application Priority Data

Oct. 9, 1997 (DE) .......................................... 197 44 621

(51) Int. Cl.⁷ .......................... A61K 33/08; A61K 6/02; C09K 3/10
(52) U.S. Cl. ........................ 424/693; 424/422; 424/423; 424/434; 424/435; 424/443; 424/445; 424/446; 424/692; 424/722; 522/908; 106/35; 433/228.1
(58) Field of Search ................................ 424/443, 445, 424/446, 693, 692, 722, 422, 423, 434, 435; 522/908; 106/35; 433/228.1

(56) References Cited

U.S. PATENT DOCUMENTS

| | | | | |
|---|---|---|---|---|
| 4,082,558 A | * | 4/1978 | Nobuo ......................... | 106/10 |
| 4,161,410 A | * | 7/1979 | Pellico ......................... | 106/35 |
| 4,311,528 A | * | 1/1982 | Dietz et al. ................... | 106/35 |
| 4,390,033 A | * | 6/1983 | Khalil et al. .................. | 424/71 |
| 6,457,592 B1 | * | 4/1987 | Takubo ......................... | 106/35 |
| 4,740,245 A | * | 4/1988 | Futami et al. ................. | 106/35 |
| 4,931,096 A | * | 6/1990 | Fujisawa et al. ............... | 166/35 |
| 5,051,130 A | * | 9/1991 | Futami et al. ................. | 106/35 |
| 5,342,441 A | * | 8/1994 | Mandai ......................... | 106/35 |
| 5,538,728 A | * | 7/1996 | Yanaki et al. ................. | 424/401 |
| 5,540,766 A | * | 7/1996 | Castellani ..................... | 106/35 |
| 5,585,117 A | * | 12/1996 | Dietz .......................... | 424/693 |

OTHER PUBLICATIONS

Remington: The Science and Practice of Pharmacy, p. 1400, 1995.*

* cited by examiner

Primary Examiner—Jean F. Vollano
Assistant Examiner—S Sharareh
(74) Attorney, Agent, or Firm—Medlen & Carroll LLP

(57) ABSTRACT

The invention relates to a mixture for use as wound dressing, which comprises:

a) paraffins complying with DAB and/or synthetic waxes selected from the group consisting of montan waxes, petroleum waxes, Fischer-Tropsch waxes, polyolefin waxes, petrolatum, wax alcohols, and oxidates of the aforementioned substances;

b) at least one metal hydroxide.

The mixture is stable on prolonged storage at room temperature and promotes collagen regeneration in vivo in cases of bone trauma.

8 Claims, 4 Drawing Sheets

MIXTURE FOR USE AS WOUND DRESSING

The invention relates to a mixture for use as medicinal wound dressing.

The use of calcium hydroxide-containing products in dentistry is known from prior public use. They are mainly used as wound dressing, for example for managing bone traumas or for preparing a root canal filling.

DE 42 40 713 C1 discloses that a mixture of calcium hydroxide and neatsfoot oil can assist collagen regeneration in vivo. This paste according to the patent proves to be unstable on storage.

The formation of bone involves first the synthesis of organic tissue (collagen synthesis) and subsequently the incorporation, mediated by the so-called matrix vesicles, of mineral substance in the organic matrix. The connective tissue protein collagen is the main component of the organic substance of the bone. The protein consists of three helically coiled polypeptide chains whose amino-acid sequences may vary, which results in a variety of individual types of collagen. It is common to all types of collagen that the collagen fibers have exceptionally high mechanical strength. This strength is produced by a multiplicity of intra- and intermolecular linkages of the peptide chains, which in this way form the dense collagen fiber network of the connective tissue. These linkages are produced by oxidation of lysine and subsequent reaction of the aldehyde which is formed with free amino groups on adjacent chains. In addition hydrogen bonds and ester linkages with sugar residues occur. The bony tissue is formed by the incorporation of mineral substances (hydroxyapatite, calcium phosphate) in this network.

Mixtures of calcium hydroxide and neatsfoot oil are also used as root canal fillings (DE 29 32 738 C2) and, mixed with carboxylate cements, as component of temporary fixing means for provisional coverings of tooth stumps (DE 34 13 864 C1). In both cases, the prophylactic effect of calcium-hydroxide on pulpitis is made use of. The neatsfoot oil on the one hand is used as pasting auxiliary, and on the other hand delays the release of the calcium ion and the increase in the pH.

DE 40 40 713 C1 discloses that calcium hydroxide and neatsfoot oil in a mixture are unstable on storage and must be mixed immediately before use. On prolonged storage of the mixture there is hydrolysis of the neatsfoot oil.

The invention is based on the object of providing a mixture for use as wound dressing which is stable on storage in the state ready for application. The invention provides a mixture for use as wound dressing which comprises the following constituents:

a) paraffins complying with DAB and/or synthetic waxes selected from the group consisting of montan waxes, petroleum waxes, Fischer-Tropsch waxes, polyolefin waxes, petrolatum, wax alcohols, and oxidates of the aforementioned substances;

b) at least one metal hydroxide.

The mixture according to the invention contains no neatsfoot oil (oleum pedum tauri).

Concerning the definition of the waxes used according to the invention, reference is made to Ullmanns Enzyklopädie der technischen Chemie [Ullmann's Encyclopedia of Industrial Chemistry], 4th edition, Verlag Chemie, Weinheim, volume 24, pages 16–45. By oxidates of these synthetic waxes are meant those substances in which oxygen functionalities (for example carboxyl, ester, carbonyl or hydroxyl groups) have subsequently been introduced into the wax molecules. This can take place for example by reacting the melt with atmospheric oxygen. For details thereof, reference is likewise made to the section in Ullmann which has been mentioned. It may also be noted that petrolatum is likewise to be regarded as a synthetic wax (see Ullmann loc. cit.).

Surprisingly, a mixture according to the invention is stable on storage. However, in the same manner as a mixture of calcium hydroxide and neatsfoot oil, it delays the release of alkalinity, which can stimulate collagen regeneration in vivo and/or display a prophylactic actic effect on the pulp.

The term "wound dressing" is to be understood to have a wide meaning for the purpose of the invention and embraces, in particular, uses in oral surgery, implanology, traumatology or the like, in which the mixture according to the invention is applied on or in bone traumas such as, for example, fracture surfaces, drillings, cavities or the like. The term embraces, for example, root filling and use in the framework of fixing temporary coverings for tooth stumps.

Synthetic waxes which are preferred for the purpose of the invention are petrolatum and paraffins which are liquid at room temperature and comply with DAB (Deutsches Arzneimittelbuch [German Pharmacopeia]), for example paraffinum liquidum and paraffinum perliquidum.

The mixture according to the invention may additionally comprise vegetable oils, fats or waxes (esters of long-chain carboxylic acids with long-chain alcohols). These additional substances may be of assistance in particular in adjusting the consistency of the normally pasty mixture. Examples of suitable vegetable waxes are carnauba waxes, candelilla waxes, ouricury waxes, sugarcane waxes, retamo waxes and also jojoba oil.

By fats and oils are meant substances which comprise triglycerides, diglycerides and/or monoglycerides as essential constituents. Concerning suitable vegetable fats and oils, reference is made to Ullmanns Enzyklopädie der technischen Chemie, 4th edition, Volume II, pages 500–515. Very suitable examples are sunflower oil and castor oil.

Where the vegetable oils, fats or waxes show a certain tendency to hydrolysis in the presence of a metal hydroxide, which would be intrinsically deleterious for adequate stability on storage, surprisingly the synthetic waxes or their oxidates present in the mixture according to the invention stabilize the complete mixture, leading to adequate stability on storage.

The mixture preferably comprises jojoba oil, castor oil, corn oil, carnauba wax and/or sunflower oil. Preferred metal hydroxides are alkali metal and/or alkaline earth metal hydroxides, and magnesium and/or calcium hydroxides are particularly preferred. The content of the metal hydroxide or metal hydroxides in the mixture is preferably 10–75% by weight.

Where the mixture according to the invention comprises vegetable oils, fats and/or waxes, the content thereof is preferably 10–60% by weight. The content of synthetic waxes and/or their oxidates is preferably between 10 and 50% by weight.

The mixture according to the invention may comprise additional bulking agents. Suitable examples are the glasses or glass ceramics customary in the dental sector, in particular barium or strontium glasses or ionomer glasses. Also suitable is the glass ceramic fiber material which is known under the name PRIMM (polymeric rigid inorganic matrix material) (Leinfelder, JA-DA, 128 (1997) 573 et seq.).

The list of ingredients mentioned for the mixture is not necessarily exclusive. For example, it is possible in addition to add oxidation inhibitors such as 2,6-di-tert-butyl-4-methylphenol. Other biologically compatible additives and auxiliaries may likewise be added. For example, if necessary, radiopacity can be achieved by adding substances such as barium sulfate.

Mixtures (normally in paste form) of required consistency and handleability can be prepared by varying the waxes, fats and oils added to the metal hydroxides, as well as the ratios of their amounts. By choosing appropriate waxes or fats and/or oils as pasting auxiliaries it is possible to prepare, for example, pastes which are suitable as root canal filling or bone wound dressing. These pastes can contribute in vivo to promoting collagen regeneration in cases of bone trauma.

The invention is illustrated hereinafter by means of examples.

Figure 1:
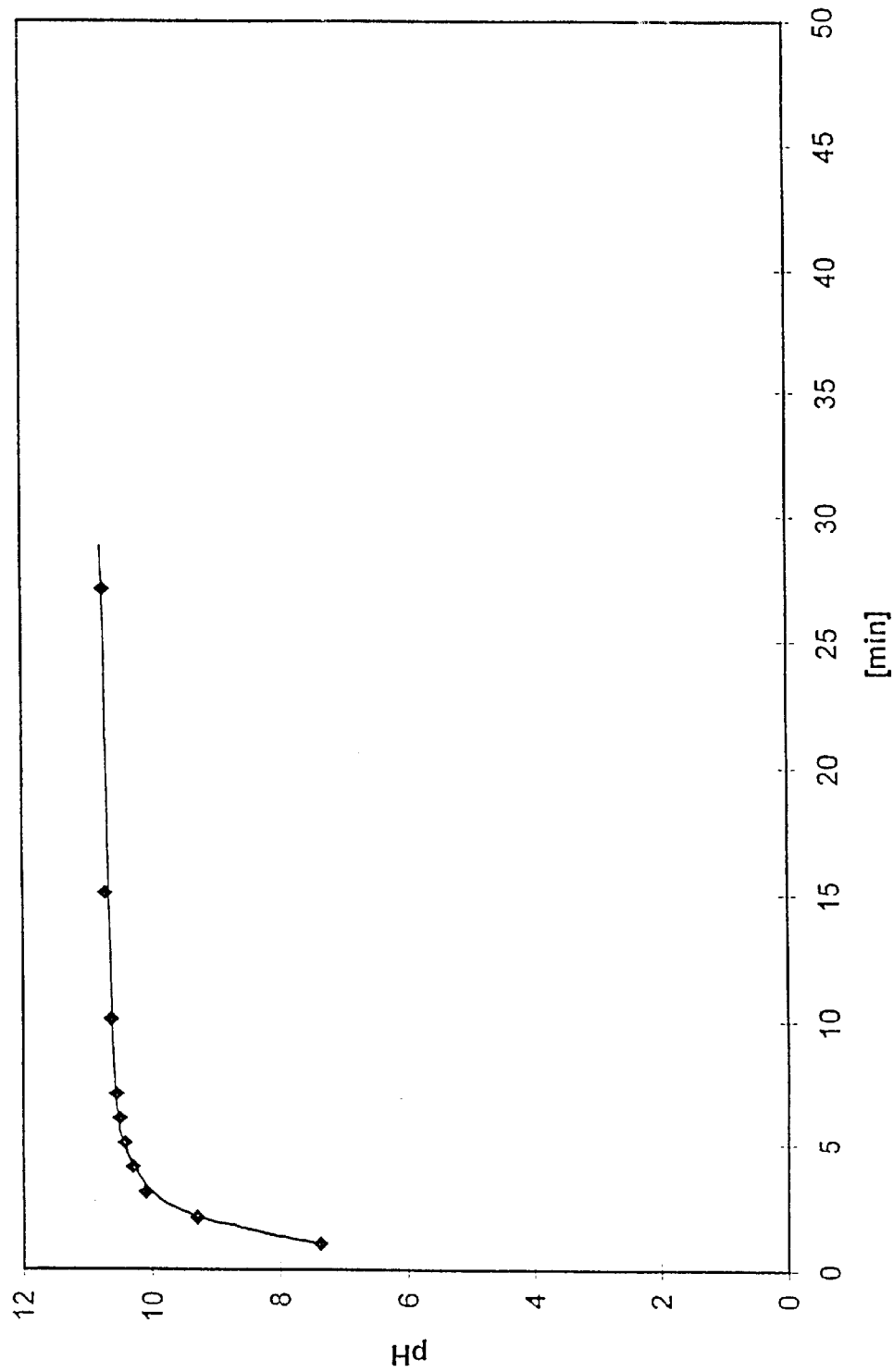
FIGS. 1 to 4 show diagrams in which the pH of the mixture according to the invention of Examples 1 to 5 in an aqueous buffer is shown as a function of time.
Figure 2:
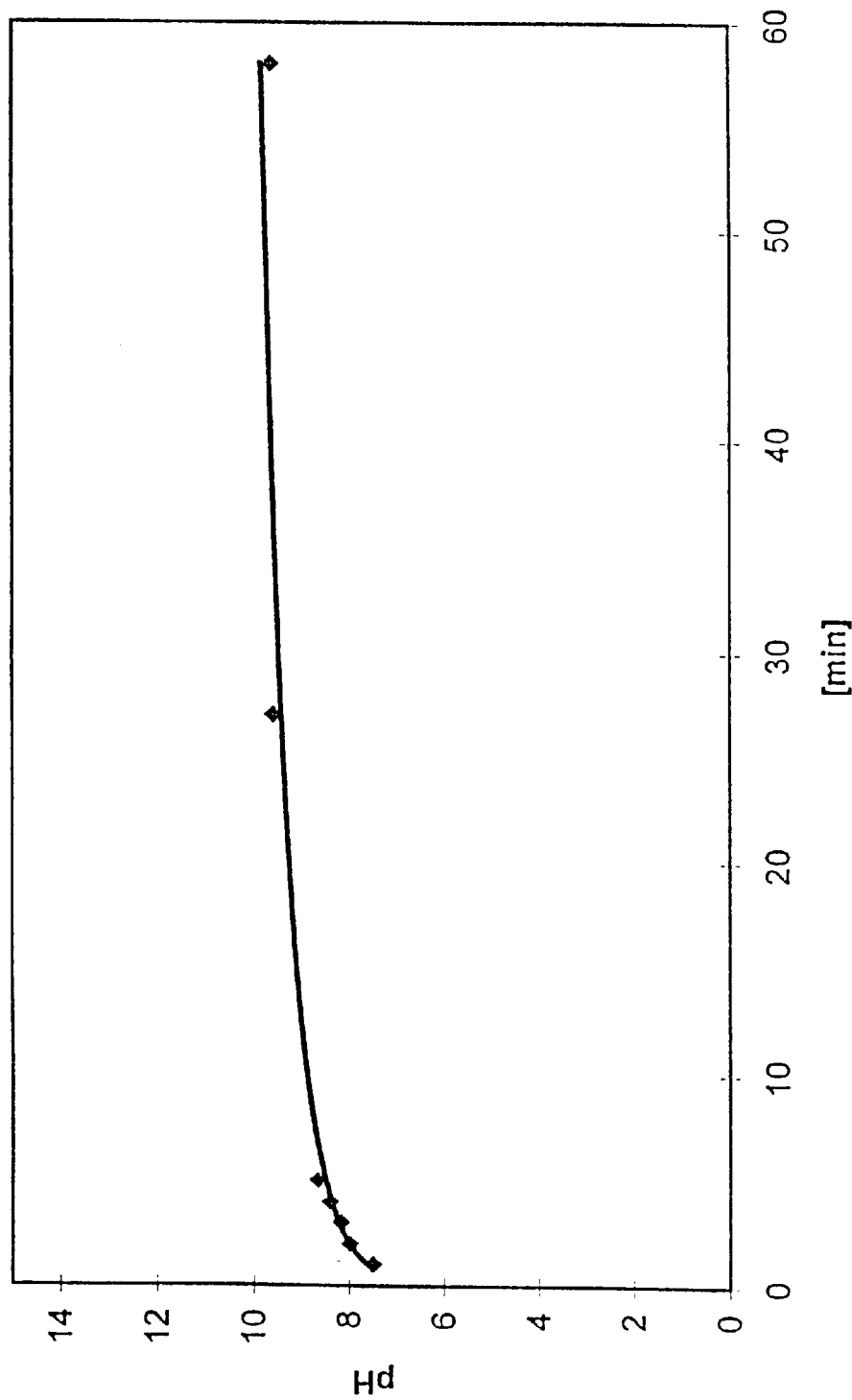
Figure 3:
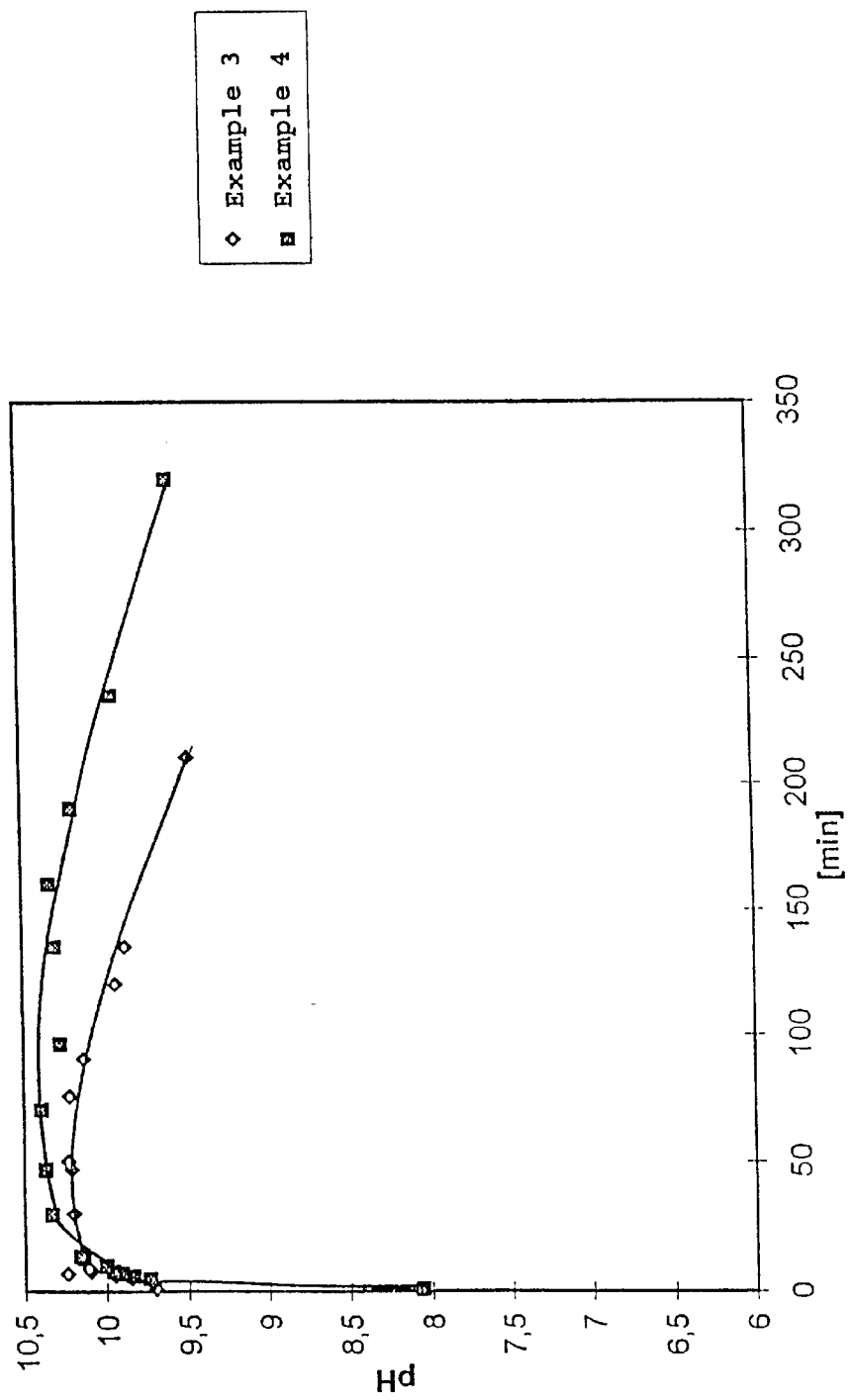
Figure 4:
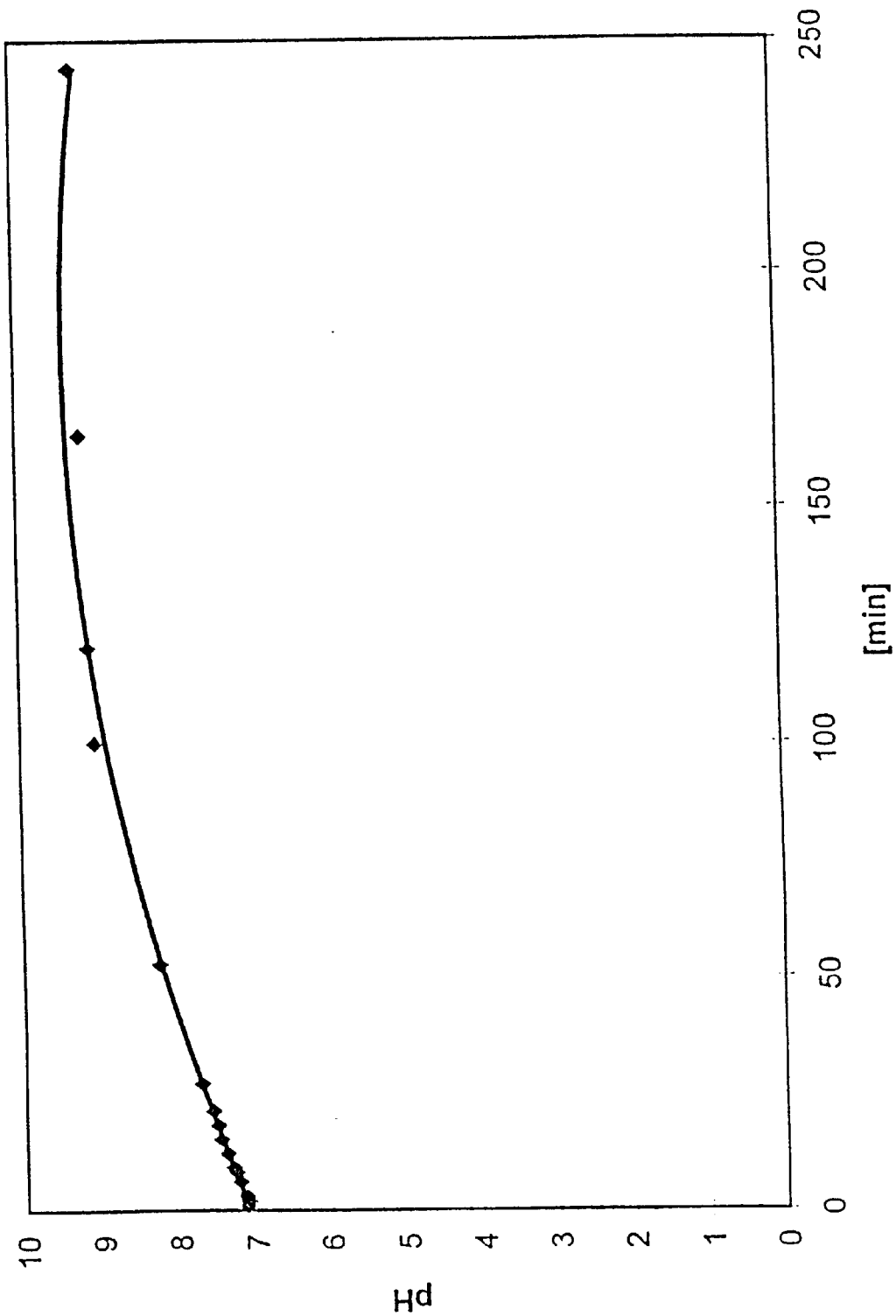

In the examples, the pH of the mixtures according to the invention is measured in a buffered aqueous solution as a function of time. This measurement is of importance for assessing the effectiveness for promoting collagen regeneration. According to DE 42 40 713 C1, application of an aqueous calcium hydroxide solution or suspension to a bone trauma results, owing to the immediate jump in pH which occurs, in necrosis of the tissue. No collagen synthesis is detectable. Collagen regeneration is, however, promoted if $Ca(OH)_2$ is slowly released and a pH of about 11, preferably 10.5, is not exceeded.

Preparation of the Buffer Solution 68 mg of imidazole are diluted with distilled water and adjusted to pH 7 with 0.1 N HCl. The volume is then made up to 1000 ml with distilled water.

EXAMPLE 1

35 g of petrolatum (DAB 10), 45 g of castor oil and 20 g of $Ca(OH)_2$ are vigorously mixed. 6 g of this mixture are stored under 30 ml of buffer, and the pH is measured.

| Time [min] | pH | Time [min] | pH |
| --- | --- | --- | --- |
| 1 | 7.38 | 6 | 10.5 |
| 2 | 9.3 | 7 | 10.55 |
| 3 | 10.1 | 10 | 10.63 |
| 4 | 10.3 | 15 | 10.71 |
| 5 | 10.42 | 27 | 10.73 |

EXAMPLE 2

35 g of petrolatum (DAB 10), 45 g of sunflower oil and 20 g of $Ca(OH)_2$ are dispersed. 6 g of this mixture are stored under 30 ml of buffer 1, and the pH is measured.

| Time [min] | pH | Time [min] | pH |
| --- | --- | --- | --- |
| 1 | 7.5 | 27 | 9.58 |
| 2 | 7.99 | 58 | 9.64 |
| 3 | 8.18 | 90 | 9.58 |
| 4 | 8.41 | 135 | 9.63 |
| 5 | 8.66 | | |

EXAMPLE 3

20 g of petrolatum (DAB 10), 20 g of jojoba oil and 60 g of $Ca(OH)_2$ are dispersed. 6 g of this mixture are stored under 30 ml of buffer 1, and the pH is measured.

EXAMPLE 4

35 g of petrolatum (DAB 10), 45 g of jojoba oil and 20 g of $Ca(OH)_2$ are dispersed. 6 g of this mixture are stored under 30 ml of buffer 1, and the pH is measured.

| Time [min] | Example 4 | Example 3 | Time [min] | Example 4 | Example 3 |
| --- | --- | --- | --- | --- | --- |
| 1 | 9.7 | 8.1 | 47 | 10.2 | 10.4 |
| 5 | 9.9 | 9.7 | 90 | 10.1 | |
| 6 | 10.0 | 9.8 | 96 | | 10.3 |
| 7 | 10.2 | 9.9 | 135 | 9.9 | 10.3 |
| 8 | 10.1 | 10.0 | 210 | 9.5 | |
| 30 | 10.2 | 10.3 | 235 | | 9.9 |

EXAMPLE 5

17 g of petrolatum (DAB 10), 17 g of sunflower oil, 66 g of $Ca(OH)_2$ and 0.1 g of 2,6-di-tert-butyl-4methylphenol are dispersed. 6 g of this mixture are stored under 30 ml of buffer 1, and the pH is measured.

| Time [min] | pH | Time [min] | pH |
| --- | --- | --- | --- |
| 1 | 7.1 | 18 | 7.5 |
| 2 | 7.1 | 21 | 7.6 |
| 3 | 7.1 | 27 | 7.7 |
| 6 | 7.2 | 53 | 8.2 |
| 8 | 7.3 | 100 | 9.0 |
| 9 | 7.3 | 120 | 9.1 |
| 12 | 7.3 | 165 | 9.2 |
| 15 | 7.5 | 244 | 9.2 |

Stability on Storage

The pastes of Examples 3 and 4 were stored in an oven at 40° C. No change in consistency was found after six months. This suggests that there is stability on storage at room temperature for more than one year.

What is claimed is:

1. A method for filling a root canal in oral surgery, comprising:
   a) providing a composition comprising at least one wax selected from the group consisting of paraffin, montan waxes, petroleum waxes, Fischer-Tropsch waxes, polyolefin waxes, petrolatum, wax alcohols, oxidates of said montan waxes, said petroleum waxes, said Fischer-Tropsch waxes, said polyolefin waxes, said petrolatum and said wax alcohols, and combinations thereof, and at least one metal hydroxide, wherein said composition does not contain neatsfoot oil, and wherein said at least one metal hydroxide exhibits a delay in alkalinity release, and wherein said composition comprises more than 20% wax by weight; and
   b) applying said composition to a root canal as a filling.
2. The method of claim 1, wherein said paraffin comprises liquid paraffin.
3. The method of claim 1, wherein said petrolatum comprises liquid petrolatum.
4. The method of claim 1, wherein said vegetable oils are selected from the group consisting of jojoba oil, castor oil, sunflower oil, and combinations thereof.
5. The method of claim 1, wherein said at least one metal hydroxide is selected from the group consisting of alkali metal hydroxide, alkaline earth metal hydroxide, and combinations thereof.

6. The method of claim 5, wherein said alkaline earth metal hydroxide comprises calcium hydroxide.

7. The method of claim 6, wherein said calcium hydroxide content is 10–75% by weight of said composition.

8. The method of claim 1, wherein said composition further comprises at least one filler.

* * * * *

UNITED STATES PATENT AND TRADEMARK OFFICE
CERTIFICATE OF CORRECTION

PATENT NO.    : 6,541,040 B2
DATED         : April 1, 2003
INVENTOR(S)   : Wolfgang Mühlbauer and Rainier Lück It is certified that error appears in the above-identified patent and that said Letters Patent is hereby corrected as shown below:

<u>Title page,</u>
Item [75], should read:
-- Inventors:    Wolfgang Mühlbauer, Hamburg (DE)
                 Rainer Lück, Tornesch (DE) --

Signed and Sealed this

Eleventh Day of May, 2004

JON W. DUDAS
*Acting Director of the United States Patent and Trademark Office*